(12) United States Patent
Gebauer

(10) Patent No.: US 9,279,789 B2
(45) Date of Patent: *Mar. 8, 2016

(54) CHROMATOGRAPHY COLUMN DISTRIBUTION SYSTEM

(71) Applicant: GE HEALTHCARE BIO-SCIENCES AB, Uppsala (SE)

(72) Inventor: Klaus Gebauer, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 14/625,497

(22) Filed: Feb. 18, 2015

(65) Prior Publication Data

US 2015/0160170 A1    Jun. 11, 2015

Related U.S. Application Data

(63) Continuation of application No. 12/420,408, filed on Apr. 8, 2009, now Pat. No. 8,986,543, which is a continuation of application No. 10/571,194, filed as application No. PCT/EP2004/010599 on Sep. 22, 2004, now Pat. No. 7,534,345.

(30) Foreign Application Priority Data

Sep. 23, 2003  (GB) .................................. 0322144.7

(51) Int. Cl.
*G01N 30/60* (2006.01)
*B01D 15/14* (2006.01)

(52) U.S. Cl.
CPC ............ *G01N 30/6017* (2013.01); *B01D 15/14* (2013.01); *Y10T 137/6851* (2015.04)

(58) Field of Classification Search
CPC ............... G01N 30/6017; B01D 15/14; Y10T 137/6851
USPC ........... 210/656, 658, 659, 198.2, 198.3, 456; 96/105, 107
See application file for complete search history.

(56) References Cited

U.S. PATENT DOCUMENTS 4,673,507 A   6/1987 Brown
4,894,152 A   1/1990 Colvin, Jr. et al.

(Continued)

FOREIGN PATENT DOCUMENTS

JP         62-53342        4/1987
WO    WO 03/005018       1/2003
WO    WO 2004/095019    11/2004

*Primary Examiner* — Ernest G Therkorn
(74) *Attorney, Agent, or Firm* — Parks Wood LLC

(57) ABSTRACT

A chromatography column distribution system includes a set of first bed support ribs extending radially from an inner, first radial position near the centre of the plate to an outer radial position nearer to the periphery of the plate and at least one set of intermediate bed support ribs starting at an intermediate radial position and extending to an outer radial position nearer to the periphery of the plate. Channels are formed between adjacent bed support ribs. The desired local effective channel height varies in accordance with a predetermined formula from the first radial position to the outer radial position. The transverse cross-sectional areas of the ribs or the channels are adapted such that the actual local effective channel height is within 15% of the desired local effective channel height over portions of the distribution system situated between the first radial position and the outer radial position. The length of the portions correspond to at least 80% of the distance between the first and outer radial position and the outer radial position.

6 Claims, 7 Drawing Sheets

(56) References Cited

U.S. PATENT DOCUMENTS

| | | |
|---|---|---|
| 5,324,426 A | 6/1994 | Joseph et al. |
| 6,224,760 B1 | 5/2001 | Davies et al. |
| 7,534,345 B2 * | 5/2009 | Gebauer ............ 210/198.2 |
| 8,986,543 B2 * | 3/2015 | Gebauer ............ 210/198.2 |
| 2002/0125181 A1 | 9/2002 | Pichl et al. |

* cited by examiner

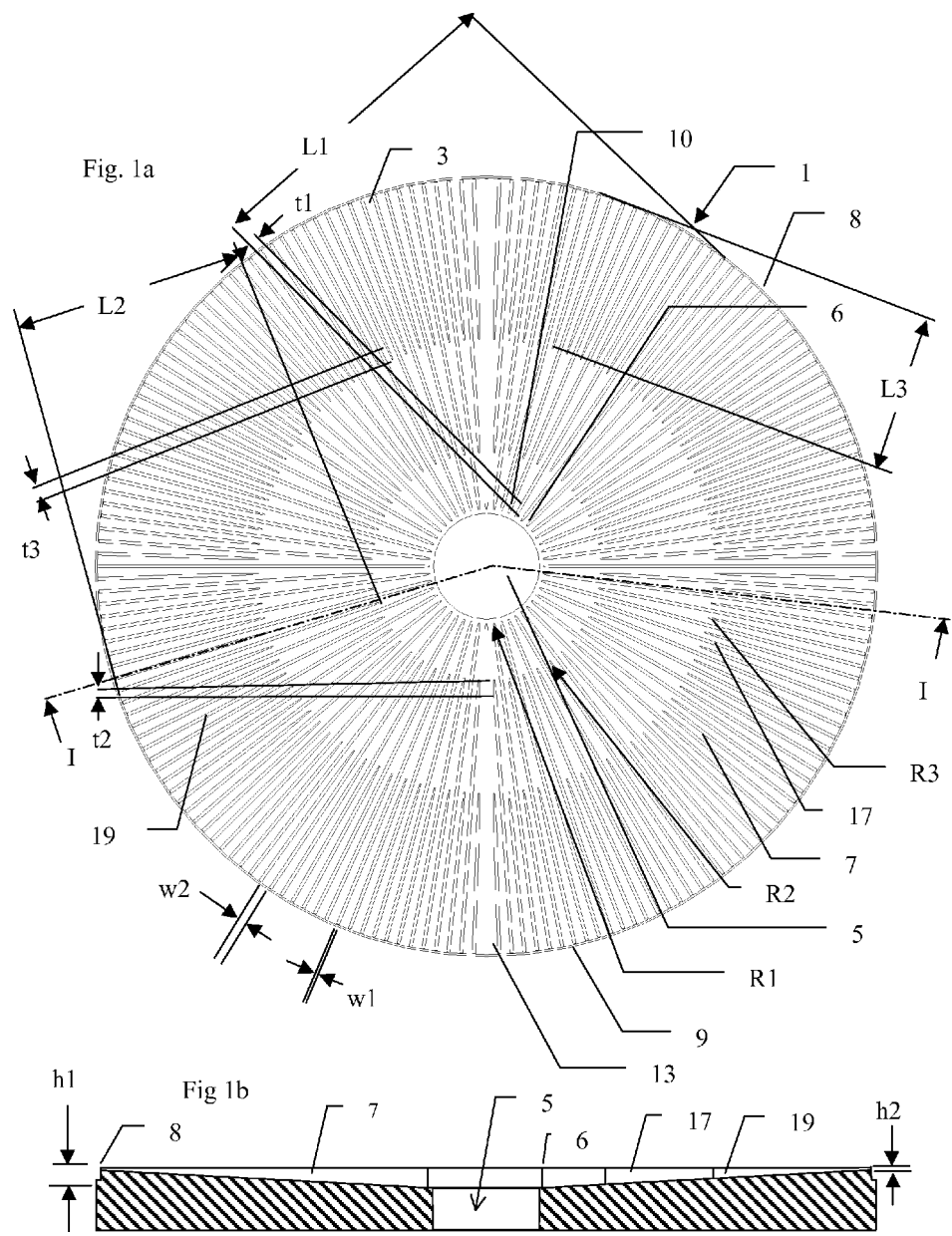

CHROMATOGRAPHY COLUMN DISTRIBUTION SYSTEM

CROSS-REFERENCE TO RELATED APPLICATIONS

This application is a continuation of U.S. patent application Ser. No. 12/420,408, filed Apr. 8, 2009 now U.S. Pat. No. 8,986,543, which is a continuation of U.S. patent application Ser. No. 10/571,194 filed Mar. 8, 2006, now U.S. Pat. No. 7,534,345, issued May 19, 2009, which is a filing under 35 U.S.C. §371 and claims priority to international patent application number PCT/EP2004/010599 filed Sep. 22, 2004, published on May 31, 2005, as WO 2005/028064, which claims priority to patent application number 0322144.7 filed in Great Britain on Sep. 23, 2003, the disclosures of which are incorporated herein by reference in their entireties.

FIELD OF THE INVENTION

The present invention relates to a liquid distribution system for chromatography columns. More specifically, the invention relates to a scalable liquid distribution system for large-scale chromatography columns.

BACKGROUND OF THE INVENTION

In separation procedures, particularly in liquid chromatography, the fluid distribution system is critical to the overall performance, and becomes more so as the cross-section of the chromatographic column increases.

Columns used in liquid chromatography typically comprise a body-forming structure enclosing a porous media through which a carrier liquid flows, with separation taking place by material distribution between the carrier liquid and solid phase of the porous media. Typically, the porous media is enclosed in the column as a packed bed, typically formed by consolidating a suspension of discrete particles. An alternative to the packed bed is the so-called expanded or fluidised bed, where effective porosity and volume of the expanded bed depends on the fluid velocity. The term 'packing' shall be used in the following to describe the porous solid phase in all types of chromatography. The efficiency of the chromatographic separation relies in both modes strongly on the liquid distribution and collection system at the fluid inlet and outlet of the packing.

Ideally, the carrier liquid is uniformly introduced throughout the surface at the top of the packing, flows through the packing at the same linear velocity throughout the packing cross section, and is uniformly removed at the plane defined by the bottom of the packing.

Conventional distribution systems for use in liquid chromatography must address a number of inherent problems that have deleterious effects on the separation efficiency of the column. Among these problems is non-uniform initial fluid distribution at the top of the packing as well as non-uniform fluid collection at the outlet of the packing. The problem of non-uniform initial fluid distribution refers generally to the problem of applying a sample volume simultaneously over the cross-sectional area of the packing. Without a simultaneous introduction of fluid in the plane defined by the top of the packing, it is virtually impossible to achieve uniform flow distribution through the packing.

This will lead to increased dispersion in the chromatographic system by broadening the convective residence time distribution of a tracer substance transported with the fluid throughout the system. The dispersion generated by the liquid distribution system has to be controlled in relation to the amount of dispersion introduced by the chromatographic packing itself by means of diffusion and mixing effects.

Standard fluid distribution systems consist of one central inlet, formed in the end plate of the column, for the mobile phase in combination with a thin distribution channel (gap) behind the filter (woven net or sinter) or bed support at the inlet end of the column and a similar fluid collection system at the outlet end of the column. The filter or bed support is supported by ribs which extend from the inner surface of the end plate to side of the filter or bed support facing the end plate. The ribs extend radially and the spaces between the ribs form distribution channels for distributing the fluid. Each rib has a tapered end section facing the centre of the column and a body of substantially constant width extending from the tapered section to the wall of the column. At given radial positions, the number of ribs doubles in order to maintain the necessary mechanical support of the filter/bed support. In columns, the local effective cross-sectional area for fluid flow in the distribution channels at a radial position r is defined by the depth of the channels h, the width of the channels w and the number of channels. The local effective channel height (i.e. the height at a location at a given radial distance from the centre of the column) for fluid flow in a column is defined as the local height of a corresponding open channel (i.e. a rib-free channel) having the same cross-sectional area for fluid flow as the total cross-sectional area of the channels in the actual column at the same radial distance. Thus, if in a particular column the channel height at a distance R from the column centre was 4 mm and half of the cross-sectional area was occupied by ribs at distance R, then the effective channel height at distance R would be 2 mm. It is considered desirable that the local effective channel height varies linearly from the centre of the column to the column wall in order to give the desired fluid distribution over the filter or bed support. However, in the prior art, no account has made of the effect that the size and number of ribs has on the local effective channel height. This can be seen in FIG. 3 in which the solid line shows the calculated effective channel height (ECH) against radial distance (R) from the centre of the column for a typical prior art column with ribs starting at R=55 mm and R=110 mm, while the dotted line shows the desired linear variation in local effective channel height. At R=55 mm the actual local effective channel height is 3.2 mm while the desired local effective channel height is 3.8 mm, i.e. only 84% of the desired value, and at R=112 mm the actual local effective channel height is 1.4 mm—only 56% of the desired height is 2.5 mm. Clearly, there is a local decrease in the effective channel height, and therefore throttling of the flow in the distribution channels, at the radial positions where the number of ribs doubles. This causes a local pressure increase which has a negative impact on the chromatographic performance.

SUMMARY OF THE INVENTION

According to the present invention, at least some of the problems with the prior art are solved by means of a device having the features present in the characterising part of claim 1.

BRIEF DESCRIPTION OF THE FIGURES

FIG. 1a) shows schematically a plan view of a prior art distribution plate for a chromatography column;

FIG. 1b) shows a cross-section along line I-I in FIG. 1a);

DETAILED DESCRIPTION OF THE INVENTION

Figure 1C:
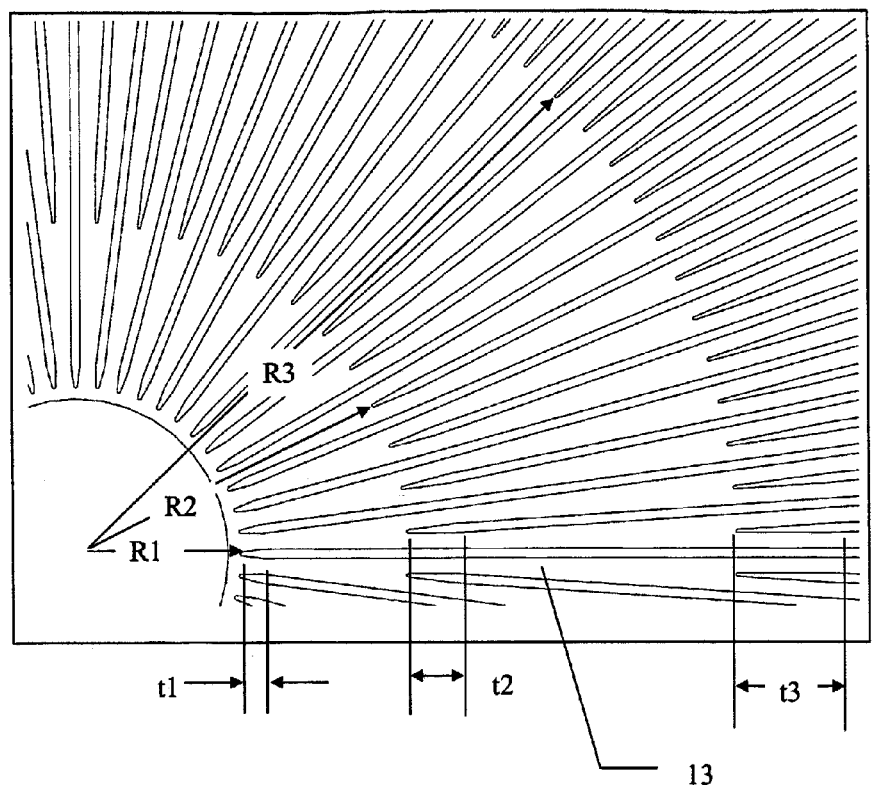
FIG. 1c) shows an enlarged view of a portion of the plan view of FIG. 1a)
Figure 1D:
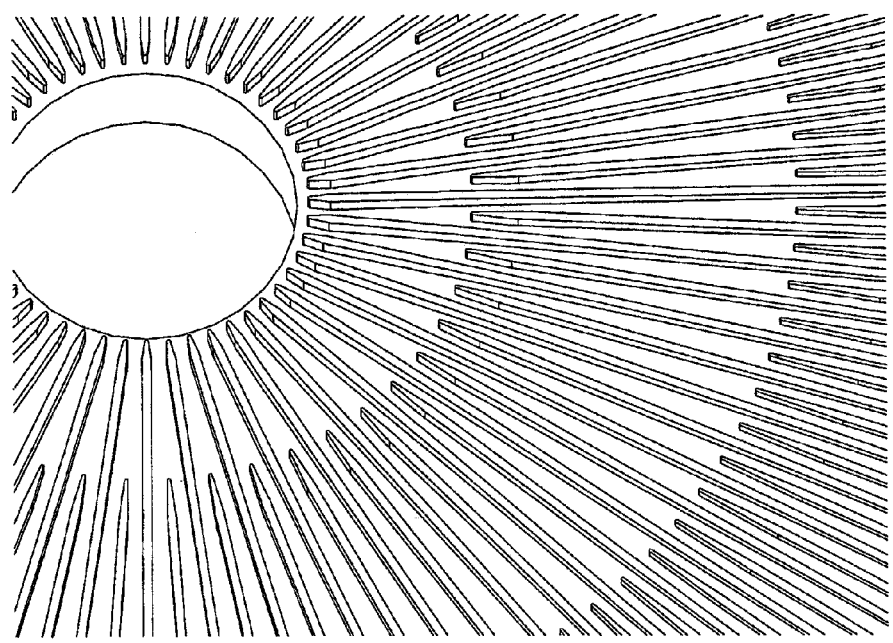
FIG. 1d) shows a perspective view of the portion of the prior art distribution plate shown in FIG. 1c)

FIGS. 1a)-1d) show schematically views of a prior art distribution system. Distribution plate 1 comprises a body 3 in the form of a disc with a central inlet orifice 5. A plurality of first bed support ribs 7 of length L1 extend radially from the region at a distance R1 from the centre of the surrounding the orifice 5 to substantially the periphery 9 of the body 3. Each first bed support rib 7 has a maximum height h1 at its first end 6 near to or at the orifice 5 and a minimum height h2 at its second end 8 near to or at the periphery 9 of the body 3. The height of the each first bed support rib 7 varies linearly from the first end 6 to the second end 8. Each first end 6 is tapered with a tapered portion 10 of length t1 facing towards the central inlet orifice 5. Each first rib has an elongated rib body 11 of length (L1–t1) with a substantially constant width w1 between the tapered portion 10 of each first end 6 and the second end 8.

Starting at a first intermediate radial position R2 situated between the orifice 5 and the periphery 9, a plurality of second, intermediate, bed support ribs 17 of length L2 which is less than L1 are positioned between the first bed support ribs 7. Each second bed support rib 17 has a tapered portion 16 of length t2 which faces towards the central inlet orifice 5, and an elongated rib body 18 of length (L2–t2) with a substantially constant width w1. These second bed support ribs 17 extend from first intermediate radial position R2 to substantially the periphery 9 of the body 3.

Starting at a second intermediate radial position R3 situated between the orifice 3 and the periphery 9 at a distance greater than R2 from the orifice 3, a plurality of third, intermediate, bed support ribs 19 of length L3 are positioned between the first bed support ribs 7 and the second bed support ribs 17. Each third bed support rib 19 has a tapered portion 21 of length t3 which faces towards the central inlet orifice 5, and an elongated rib body 23 of length (L3–t3) with a substantially constant width w1. These third bed support ribs 19 extend from second intermediate radial position R3 to near to the periphery 9 of the body 3.

Channels 13 are formed by the gaps between the ribs 7, 17, 19.

As can be understood from the FIGS. 1a)-1d), at the regions in the vicinity of the radial positions R2 and R3 there is a reduction in the local cross-sectional area of the channels 13 due to the presence of the second, respectively, third support ribs. This reduction in the local cross-sectional area causes a local throttling of the flow though the channels 13 which is manifested as a local pressure increase. This disturbs the flow through the distribution system and has a negative impact on the performance of the chromatography column.

Figure 2A:
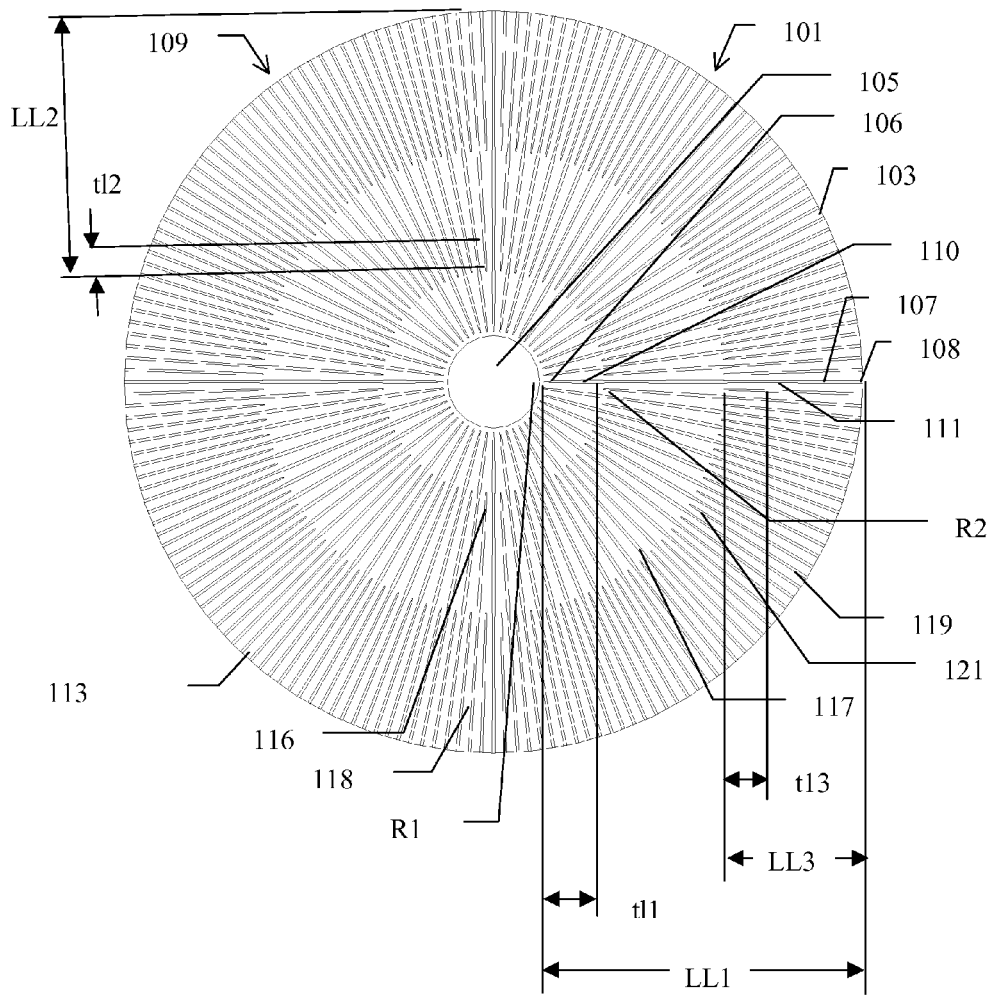
FIG. 2a) shows schematically a plan view of a first embodiment of a chromatography column distribution plate in accordance with the present invention.
Figure 2B:
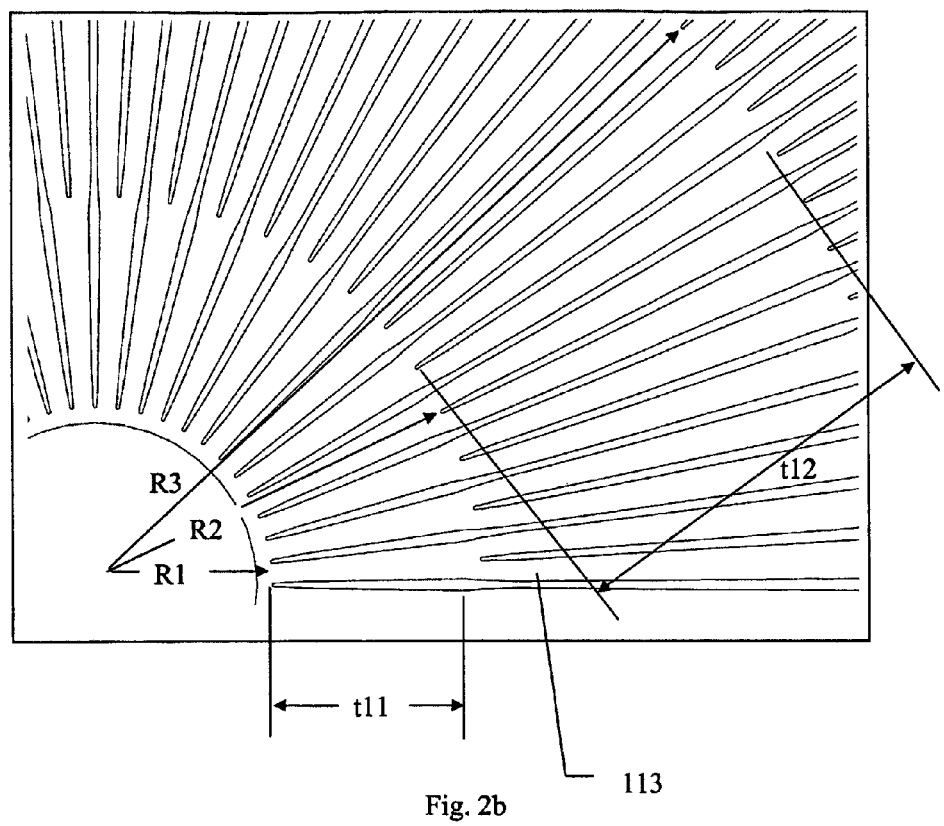
FIG. 2b) shows an enlarged view of a portion of the plan view of FIG. 2a)
Figure 2C:
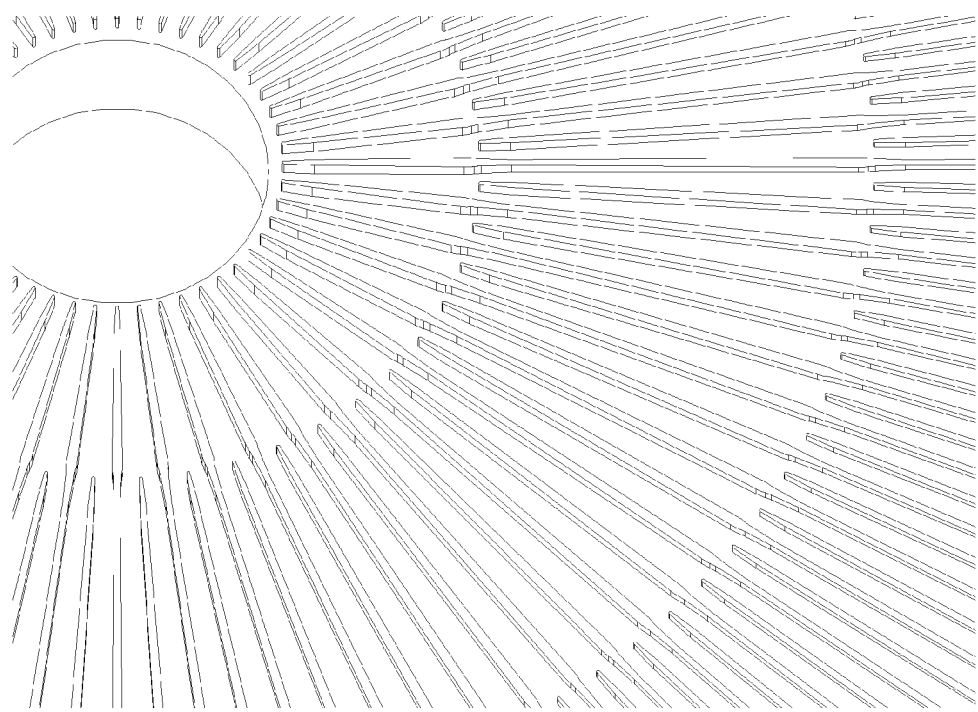
FIG. 2c) shows a perspective view of the portion of the prior art distribution plate shown in FIG. 2b)
Figure 3:
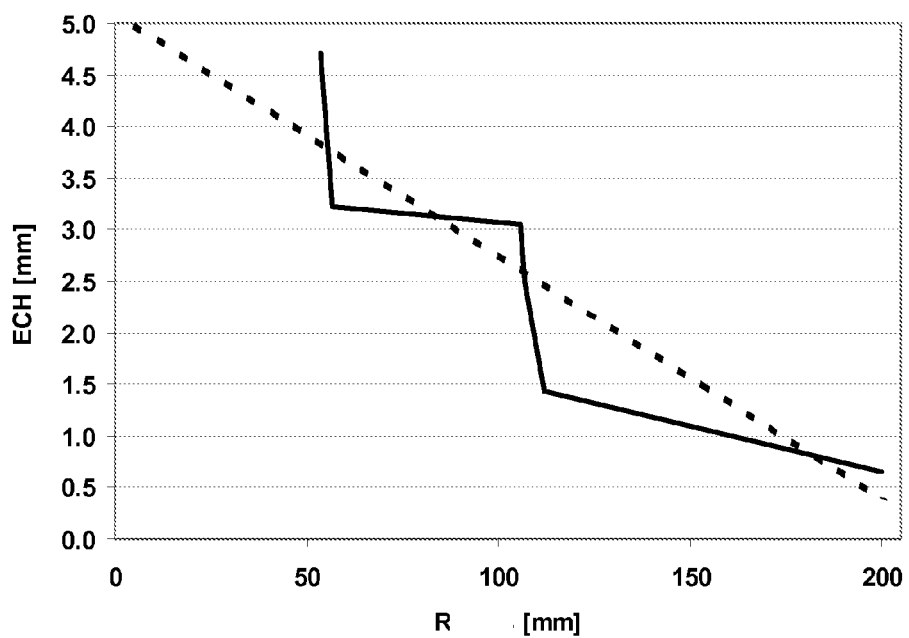
FIG. 3 is a graph showing effective channel height (ECH) against radial distance (R) for a prior art column; and, FIG. 4 is a graph showing effective channel height (ECH) against radial distance (R) for an embodiment of a column in accordance with the present invention.

FIGS. 2a)-2c) show schematically views of a first embodiment of a distribution plate 101 in accordance with the present invention. Distribution plate 101 comprises a body 103 in the form of a disc with a central inlet orifice 105. A plurality of first bed support ribs 107 of length LL1 extend radially from an inner, first radial position R1 near to the orifice 105 to an outer radial position near to the periphery 109 of the body 103. Each first bed support rib 107 has a maximum height at its first end 106 near to or at the orifice 105 and a minimum height at its second end 108 near to or at the periphery 109 of the body 103. The height of the each first bed support rib 107 varies linearly from the first end 106 to the second end 108. Each first end 106 is tapered with a tapered portion 110 of length t11 facing towards the central inlet orifice 105. Each first rib 107 has an elongated rib body 111 of length (LL1–t11) which extends from the point of maximum width of the tapered portion 110 to the second end 108. As explained below, elongated rib 111 body does not have a constant width along its length.

Starting at a first inner intermediate radial position R2 situated between the orifice 105 and the periphery 109, a plurality of first intermediate bed support ribs 117 of length LL2 (which is less than LL1) are positioned between the first bed support ribs 107. Each first intermediate bed support rib 117 has a tapered portion 116 of length t12 which has a pointed end that faces towards the central inlet orifice 105, and an elongated rib body 118 of length (LL2–t12) with a varying width as described below. These first intermediate bed support ribs 117 extend from first intermediate radial position R2 to the outer radial 10 position near to the periphery 109 of the body 103.

Starting at a second inner intermediate radial position R3 situated between the orifice 105 and the periphery 109 at a distance greater than R2 from the orifice 103, a plurality of second intermediate, bed support ribs 119 of length LL3 are positioned between the first 15 bed support ribs 7 and the first intermediate bed support ribs 117. Each second bed support rib 119 has a tapered portion 121 of length t13 which has a pointed end that faces towards the central inlet orifice 105, and an elongated rib body 123 of length (LL3–t13) with a varying width. These second intermediate bed support ribs 119 extend from second inner intermediate radial position R2 to the outer radial position near to the periphery 109 of the body 103.

Channels 113 are formed by the gaps between the ribs 107, 117, 119. In this embodiment the local effective channel height decreases in a more linear manner than in prior art devices (i.e. the maximum difference between the desired local effective channel height and the actual local effective channel height is less than 15.5% of the desired local channel height) from the position R1 to the periphery of the column). This is achieved by the widths of the elongated rib bodies 111, 118 and 123 being varied along their lengths in order to reduce or eliminate discontinuities (that is, abrupt local changes) in the cross sectional area of the channels 113 formed between ribs. This may be achieved by adapting the width of the elongated body 111 of each first support rib 107 at the position along its length where it is adjacent the tapered portion 116 of a first intermediate support rib 117 and/or second intermediate support rib 119 and/or by adapting the width of the elongated body 118 of each first intermediate support rib 117 at the position along its length where it is adjacent the tapered portion 121 of a second intermediate support rib 119 so that the actual local effective channel height is at worst within 15% of, preferably is within 10% of, more preferably is within 5% of, and most preferably is the same as the desired local effective channel height. In order to reduce discontinuities in the cross sectional area of a channel at the radial positions where there are first and second intermediate support ribs 117, 119, the width of each elongated body 111 at any radial position is the adapted to partly or completely compensate for the reduction in channel cross sectional area caused by the presence of the intermediate support rib 117 so that the actual local effective channel height is at worst within 15% of the desired local channel height. Preferably the actual local effective channel height is within 10% of, more preferably it is within 5% of, and most preferably is the same as the desired local effective channel height over most of the length of the longest ribs. This is achieved by adapting the tangential cross sectional area of each elongated rib body 111 at a radial position Rx by an amount equal to, or slightly more than, or slightly less than, the tangential cross sectional area of an adjacent intermediate support rib 117 at the same radial position Rx. In this embodiment of the present invention, in order to keep the cross sectional area of a channel constant at the radial positions where there are first, first intermediate and second intermediate support ribs, the reduction in channel cross sectional area caused by the presence of a second intermediate support rib 119 is compensated for by adapting the widths of both first and first intermediate support ribs 107 and 117 equally at every radial position Rx by an amount equal to half of the reduction in channel cross sectional area caused by the presence of a second intermediate support rib 117.

Figure 4:
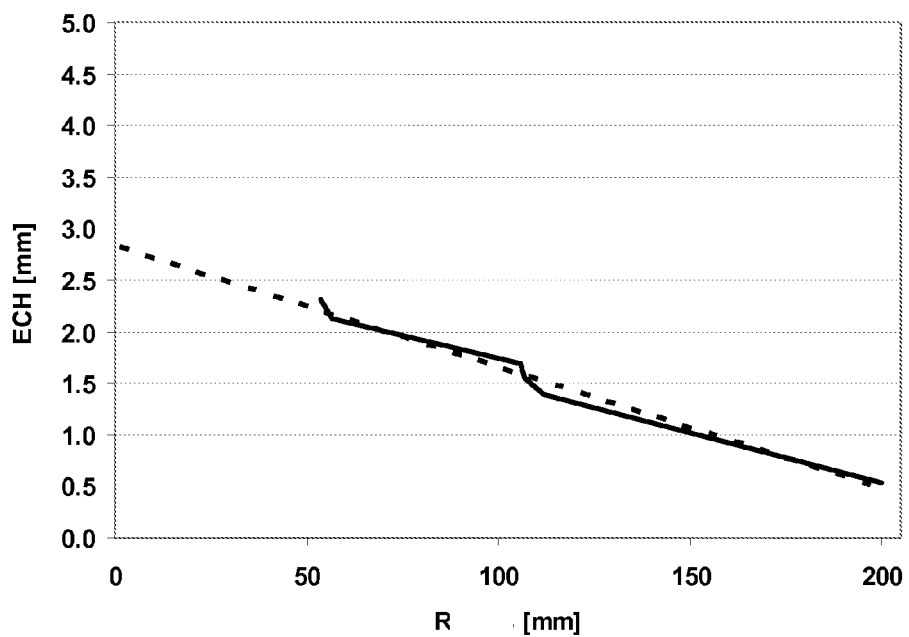

FIG. 4 is a graph showing the local effective channel height (ECH) against radial position (R) for a column distribution system in accordance with the present invention in which the distribution system has two sets of ribs—the first set starting at R=55 mm and the second set starting at R=110 mm. as can be seen in FIG. 4. In FIG. 4 the maximum deviation of the actual local effect column height (shown by a solid line) from the desired local effective column height (shown by a dotted line) occurs at R=110 m where the actual effective channel height is 1.6 mm and the desired effective channel height is 1.5 15 mm—a difference of only 6.7%. In this column, over the length of the longest ribs, the lengths of the portions of the channels which have an actual local effective channel height that is within 5% of the desired local effective channel height, when added together, correspond to more than 80% of the length of longest of these ribs.

Preferably, distribution systems in accordance with the present invention are machined so that the portions of the distributions system where the actual local effective channel height is within 5% of the desired local effective channel height correspond to more than 90% of the length of the longest ribs. More preferably, distribution systems in accordance with the present invention are machined so that the actual local effective channel height is within 5% of the desired local effective channel height for more than 95% of the length of these ribs. Most preferably, distribution systems in accordance with the present invention are machined so that the actual local effective channel height is within 5% of the desired local effective channel height for 100% of the length of these ribs.

In another embodiment of the present invention instead of compensating for the reduction of the channel width caused by the presence of a third support rib 119 by adapting the width of both elongated rib bodies 111 and 118, the width of just one type of elongated rib body, e.g. elongated rib bodies 118 can be adapted.

In a further embodiment of the present invention, instead of compensating for the reduction of the channel width caused by the presence of a second and further support ribs by adapting the width of longer rib bodies, the height of the channel between the ribs can be adapted.

While the present invention has been illustrated by examples of embodiments of distribution systems for columns in which the local effective channel is intended to vary linearly in the radial direction (i.e. local effective column height is proportional to the inverse of the radial distance from the centre of the column), it is also conceivable to apply the present invention to distribution systems for columns where the local effective channel height is not intended to vary linearly but in a curve in accordance with another formula, for example, local effective column height is proportional to the inverse of the square of radial distance from the centre of the column.

By increasingly accurately adapting the dimensions of the ribs, it is possible to achieve a distribution system in accordance with the present invention where the actual local effective channel height is within 5% of the desired channel height over the whole length of the ribs. By using highly accurate computer-controlled production methods it is possible to produce a distribution system with an actual local effective channel height that is substantially the same as the desired local effective channel height over the whole length of the ribs.

The above mentioned embodiments are intended to illustrate the present invention and are not intended to limit the scope of protection claimed by the following claims.

What is claimed is:

1. A chromatography column distribution system comprising a set of first bed support ribs having an elongated rib body characterized by a width extending radially from an inner, first radial position near the center of a plate to an outer radial position nearer to the periphery of the plate and at least one set of intermediate bed support ribs starting at an intermediate radial position of the plate and extending to an outer radial position approximately near the periphery of the plate, wherein channels are formed between adjacent bed support ribs and at least one elongated rib body width is intended to vary in accordance with a predetermined formula from said first radial position to said outer radial position for minimizing local throttling and local pressure increases, and wherein the transverse cross-sectional areas of said support ribs or said channels are adapted such that the actual local effective channel height is within 15% of the desired local effective channel height over portions of the distribution system situated between said first radial position and said outer radial position, wherein the total length of said portions correspond to at least 80% of the distance between said first radial position and said outer radial position.

2. The chromatography column distribution system of claim 1, wherein the transverse cross-sectional areas of said ribs or said channels are adapted such that the actual local effective channel height is within 10% of the desired local effective channel height.

3. The chromatography column distribution system of claim 1, wherein the transverse cross-sectional areas of said ribs or said channels are adapted such that the actual local effective channel height is within 5% of the desired local effective channel height.

4. The chromatography column distribution system of claim 1, wherein said local effective channel height varies inversely in proportion to said first radial position.

5. The chromatography column distribution system of claim 1, wherein said portions correspond to at least 90% of the distance between said first radial position and said outer radial position.

6. The chromatography column distribution system of claim 1, wherein said portions correspond to at least 95% of the distance between said first radial position and said outer radial position.

* * * * *